(12) United States Patent
Bragg et al.

(10) Patent No.: US 9,908,917 B2
(45) Date of Patent: Mar. 6, 2018

(54) **PRODUCTION OF POLYPEPTIDES RELEVANT TO HUMAN AND ANIMAL HEALTH USING *YARROWIA LIPOLYTICA***

(71) Applicant: UNIVERSITY OF THE FREE STATE, Bloemfontein (ZA)

(72) Inventors: Robert Richard Bragg, Bloemfontein (ZA); Charlotte Enastacia Boucher, Bloemfontein (ZA); Chrispian William Theron, Bloemfontein (ZA); Arina Corli Hitzeroth, Bloemfontein (ZA)

(73) Assignee: UNIVERSITY OF THE FREE STATE, Bloemfontein (ZA)

( * ) Notice: Subject to any disclaimer, the term of this patent is extended or adjusted under 35 U.S.C. 154(b) by 0 days.

(21) Appl. No.: 14/870,985

(22) Filed: Sep. 30, 2015

(65) Prior Publication Data

US 2016/0090601 A1 Mar. 31, 2016

(30) Foreign Application Priority Data

Sep. 30, 2014 (ZA) .................................. 2014/07098

(51) Int. Cl.
| | | |
|---|---|---|
| *C07K 14/005* | (2006.01) | |
| *A23L 33/18* | (2016.01) | |
| *A61K 39/12* | (2006.01) | |
| *C12N 7/00* | (2006.01) | |
| *C12N 15/81* | (2006.01) | |
| *G01N 33/569* | (2006.01) | |
| *G01N 33/68* | (2006.01) | |
| *A61K 38/00* | (2006.01) | |
| *A61K 39/00* | (2006.01) | |

(52) U.S. Cl.
CPC ............ *C07K 14/005* (2013.01); *A23L 33/18* (2016.08); *A61K 39/12* (2013.01); *C12N 7/00* (2013.01); *C12N 15/815* (2013.01); *G01N 33/56961* (2013.01); *G01N 33/6854* (2013.01); *A23V 2002/00* (2013.01); *A61K 38/00* (2013.01); *A61K 2039/523* (2013.01); *A61K 2039/552* (2013.01); *C12N 2750/10022* (2013.01); *C12N 2750/10034* (2013.01); *C12N 2750/10051* (2013.01)

(58) Field of Classification Search
None
See application file for complete search history.

(56) References Cited

U.S. PATENT DOCUMENTS

| 6,083,717 A | 7/2000 | Madzak et al. |
| 6,582,951 B1 | 6/2003 | Nicaud et al. |
| 8,323,935 B2 * | 12/2012 | Xue ............... C12N 9/0083 435/134 |
| 2002/0037292 A1 * | 3/2002 | Audonnet ............ A61K 39/12 424/186.1 |

FOREIGN PATENT DOCUMENTS

| WO | WO 96/41889 | 12/1996 |
| WO | WO 00/12729 | 3/2000 |

OTHER PUBLICATIONS

Yue et al. Journal of Microbiological Methods 72 (2008) 116-123.*
Casali, Nicola. *Escherichia coli* Host Strains. Methods in Molecular Biology, vol. 235 (p. 27-48): *E. coli* Plasmid Vectors. Edited by N. Casali and A. Preston. Humana Press Inc, Totowa, NJ. 2003.*
Ban-Zhan. Journal of Biochemistry and Molecular Biology in the Post Genomic Era, vol. 2, No. 1, 2012.*
Shin et al. Vaccine 31 (2013) 4287-4292.*
Gellissen, Gerd, et al., "New yeast expression platforms based on methylotrophic *Hansenula polymorpha* and *Pichia pastoris* and on dimorphic *Arxula adeninivorans* and *Yarrowia lipolytica*—A comparison." *FEMS Yeast Research*, Aug. 2005, 5: 1079-1096.
Nicaud, Jean-Marc, et al., "Protein expression and secretion in the yeast *Yarrowia lipolytica.*" *FEMS Yeast Research*, Apr. 2002, 2: 371-379.

* cited by examiner

*Primary Examiner* — Oluwatosin A Ogunbiyi
(74) *Attorney, Agent, or Firm* — Saliwanchik, Lloyd & Eisenschenk

(57) ABSTRACT

The present invention relates to the expression of polypeptides using *Yarrowia lipolytica*, in particular the secretion of expressed polypeptides into either the extracellular space or the surface of the *Y. lipolytica* host cell wall. The invention also extends to the use of the polypeptides so expressed in biotechnological applications. The present invention provides an expression construct for the expression of polypeptides using at least a single *Yarrowia lipolytica* yeast cell, the expression construct having at least one expression cassette, the expression cassette including an acid extracellular protease secretion signal sequence and flanking zeta sequence recombination sites.

17 Claims, 4 Drawing Sheets

PRODUCTION OF POLYPEPTIDES RELEVANT TO HUMAN AND ANIMAL HEALTH USING *YARROWIA LIPOLYTICA*

CROSS REFERENCE TO RELATED APPLICATIONS

This application claims priority to South African Application No. 2014/07098, dated Sep. 30, 2014; which is incorporated herein it its entirety.

The Sequence Listing for this application is labSeqList-30Sep15-ST25.txt", which was created on Sep. 30, 2015, and is 19 KB. The entire content is incorporated herein by reference in its entirety.

TECHNICAL FIELD

The present invention relates to the expression of polypeptides using *Yarrowia lipolytica*, and in particular the secretion of expressed polypeptides into either the extracellular space or on to the surface of the *Y. lipolytica* host cell wall. The invention also extends to, but is not limited to, the use of the polypeptides so expressed in medical and veterinary biotechnological applications.

BACKGROUND

*Y. lipolytica* is a dimorphic, aerobic yeast generally considered non-pathogenic due to its low maximal growth temperature. In light of this, it has been classified by the Food and Drug Agency as generally regarded as safe. This organism is notable for its unusual metabolism—it can metabolise few sugars but is able to break down and use a number of hydrophobic substances, including long-chain fatty acids. The organism is easy to transform, with good transformation efficiency and stability being observed. In addition, development of recombinant promoters in this organism has allowed high levels of expression to be achieved in nearly all growth mediums (Nicaud et al (2002); FEMS Yeast Research; volume 2; pg 371-379).

The use of yeasts such as *Y. lipolytica* for expression of proteins is necessary due to the inability of bacterial expression systems to perform mammalian post-translational modification of proteins.

Yeasts, along with Eukaryotic cell cultures and genetically engineered plants, are able to perform some or all of these modifications and thus produce a superior product. Yeasts, especially, have a number of advantages when used in this manner: a well-understood culture methodology, purification regime, rapid biomass conversion and the ability to perform most mammalian post-translational modifications. This facility can also be improved using genetic engineering—for instance, the insertion of human genes catalysing glycosylation—for which yeasts are also admirably suited.

However, the most commonly used representative of the yeast family—*Saccharomyces cerevisiae*—has certain limitations, such as low heterologous protein production in culture and hyperglycosylation of recombinant proteins. The potential advantages of other yeast species as expression systems, including more mammalian-like post-translational modifications of proteins and the ability to use other carbon sources, has lead research into these organisms as alternatives to *S. cerevisiae*. Four of these species; *Hansenula polymorphs, Pichia pastoris, Arxula adeninivorans* and *Yarrowia lipolytica*; were reviewed in terms of their comparative advantages and disadvantages as expression systems (Gellisen et al (2005); FEMS Yeast Research; volume 5; pg 1079-1096). In this review, *Y. lipolytica* was identified alongside *A. adeninivorans* as having promising potential for industrial processes.

Accordingly, there is a need in the art for expression systems specific to *Y. lipolytica* for the production of polypeptides with biotechnological applications.

DISCLOSURE OF THE INVENTION

For the purposes of the present specification, the term "polypeptide" as used herein is understood as denoting peptides or proteins which comprise two or more amino acids bonded via peptide bonds.

The term "fusion polypeptide" or "fusion protein" refers to a polypeptide or protein which is constituted from sequences taken from more than one other polypeptide or protein, joined contiguously so that the sequences are expressed as a single polypeptide or protein.

The term "acid extracellular protease secretion signal sequence" as used herein is understood as referring to a nucleotide sequence which, when expressed as a polypeptide in fusion with another polypeptide or protein, will direct the cell to transport the fused protein into the extracellular space.

The term "zeta sequence recombination site" or "zeta element" as referred to herein refers to nucleotide sequences in the form of Long Terminal Repeats of the Ylt 1 retrotransposon. These sequences promote homologous integration of any attached genetic sequences into the yeast host genome, so long as the host genome also contains Ylt 1 retrotransposons. The retrotransposon can also be introduced into the genome of strains devoid of zeta elements, primarily by means of non-homologous recombination and random integration The term "cell wall protein" refers to a polypeptide which, when expressed into the extracellular space by the host cell, anchors itself and any attached fusion polypeptides/proteins to the host cell wall.

The term "auxotrophic marker" refers to a nucleotide sequence which, when expressed by the host cell, allows it to manufacture a particular nutrient (usually an amino acid) endogenously. The marker serves as a positive selective aid when sequences carrying it are transformed into a host cell that is unable to manufacture the relevant nutrient.

According to a first aspect thereof, the present invention provides for a genetic construct for the expression of polypeptides in *Yarrowia lipolytica* the genetic construct including at least an acid extracellular protease secretion signal sequence and flanking zeta sequence recombination sites. In a preferred embodiment of the invention, the acid extracellular protease secretion signal is the nucleotide sequence of SEQ ID 1, or a fragment or fragments thereof. In a further preferred embodiment, the flanking zeta sequence recombination sites are the nucleotide sequence of SEQ ID 2, or a fragment or fragments thereof.

In an embodiment of the invention, the genetic construct includes at least one expression cassette, the expression cassette including the acid extracellular protease secretion signal sequence and flanking zeta sequence recombination sites. The genetic construct may further be in the form of an expression vector; typically an extrachromosomal genetic element such as a plasmid or bacteriophage genome that is used to introduce one or more genes into a host cell.

In an embodiment of the present invention, the genetic construct is a plasmid and the host cell is *Y. lipolytica*. In a preferred embodiment, the genetic construct is a plasmid which is pre-fragmented before integration with the host cell. It may be appreciated that a number of approaches may be used to fragment a plasmid. In a further preferred embodiment, the fragmentation is carried out using restriction endonucleases, as is known in the art. In a further preferred embodiment, these restriction endonclueases include, but are not limited to: SfiI, AvrII, BamHI, Acc651, KpnI, BglI, HindIII, BspEI and combinations thereof.

In an embodiment of the invention, the genetic construct may include a *Y. lipolytica* cell wall protein encoding element, located between a Multiple Cloning Site (MCS) or polypeptide encoding region and the terminator element of the expression cassette. In a preferred embodiment of the invention, the protein YI CWP110 (NCBI accession number: YALI0E18788g) of nucleotide SEQ ID 3 is used as a cell wall protein encoding element.

The expression cassette referred to herein above comprises those genetic elements which are necessary for expression and/or co-expression of the polypeptide encoding region/s in the *Y. lipolytica* yeast host cell. In particular, the expression cassette includes at least one promoter element and at least one terminator element.

In a preferred embodiment of the invention, the hp4d recombinant promoter of SEQ ID 4 is used as a promoter element.

In an embodiment of the invention, the acid extracellular protease secretion signal sequence is located between the promoter element and polypeptide encoding region or MCS. The genetic construct may further include a MCS located between the acid extracellular protease secretion signal sequence and terminator element of the expression cassette. The MCS includes multiple recognition and digestion sites for Restriction Enzymes. In an embodiment of the invention, the MCS includes sites for known Restriction Enzymes, including sites selected from among: SfiI, AvrII, BamHI, Acc651, KpnI, BglI, HindIII and BspEI.

According to a second aspect thereof, the present invention provides for a method of transforming the *Y. lipolytica* host cell with an expression construct or combinations of expression constructs, the method including the steps of:
a) optionally, modifying one or more expression constructs to include a desired nucleotide sequence of a polypeptide;
b) optionally, transforming one or more expression vectors into a non-yeast host cell;
c) optionally, modifying, isolating, and purifying of relevant fractions of the expression vector or vectors to remove bacterial moieties and/or linearise the vector resulting in one or more expression cassettes;
d) transforming the expression cassette or cassettes into a *Y. lipolytica* yeast cell; and
e) culturing the transformed yeast host cell so as to express one or more polypeptides into the extracellular space or onto the host cell wall.

It should be understood that the design of the expression construct employed in the present invention may vary, and will depend on factors such as the non-yeast host cell and transfection approach being used to transfer the expression construct and expression cassette into the host cell. For instance, the number and type components (including the expression cassette, zeta flanking regions, auxotrophic marker elements and bacterial moiety elements) may vary. In an embodiment of the invention, the non-yeast host cell is a bacterial host cell.

In a preferred embodiment of the invention, the genetic construct is the pINA1317 (see FIG. 1) or pSD (see FIG. 2) plasmid.

The expression construct may include one or more auxotrophic marker regions for the purposes of replication and selection in yeast host cells. In an embodiment of the invention, auxotrophic markers are selected from among the uracil (ura) and leucine (leu) auxotrophies. These may be used together as separate vectors in some strains to transform one such strain with more than one copy of the gene of interest or more than type of gene, encoding for different polypeptide products.

The expression construct may further include one or more bacterial moiety regions for the purposes of replication and selection in bacterial host cells. This region may then include flanking sites for Restriction Enzyme digestion, allowing excision and removal of the bacterial moiety prior to insertion of the expression construct into the yeast host cell.

In an embodiment of the invention, bacterial moieties are selected from among the bacterial antibiotic resistant gene constructs, the gene constructs including, but not limited to, constructs encoding Kanamycin resistance. In a further embodiment, the bacterial moieties include a bacterial origin of replication. The flanking Restriction Enzyme digestion site is selected from among the known restriction enzyme sites. In a preferred embodiment, the NotI site is used as a flanking Restriction Enzyme digestion site.

In an embodiment of the invention, the non-yeast host cell is of bacterial origin. The host cell is selected from the group consisting of *Eschericia coli* (*E. coli*), *Bacillus subtilis* and *Thermus thermophilus*. In an embodiment of the invention, *E. coli* JM109 (endA1, recA1, gyrA96, thi, hsdR17 ($r_k^-$, $m_k^+$), relA1, supE44, Δ(lac-proAB), [F' traD36, proAB, laqI$^q$ZΔM15]) is employed as the bacterial host cell. In a preferred embodiment, top 10 competent *E. coli* cells or XL10 gold competent *E. coli* cells may employed as the bacterial host cell.

In an embodiment of the invention, the yeast host cell is selected from the group consisting of *Y. lipolytica*: Po1h (MatA, ura3-302, xpr2-322, axp1-2); Po1f (MatA, leu2-270, ura3-302, xpr2-322, axp-2); E129 (MatA, lys11-23, ura3-302, leu2-270, xpr2-322) and E150 (MatB, his-1, leu2-270, ura3-302, xpr2-322). In a preferred embodiment of the invention, Po1h is employed as the yeast host cell.

The host cell can be transformed using the described vectors by various methods (e.g. electroporation, transfection using calcium chloride, rubidium chloride, calcium phosphate, the lithium-acetate method, DEAE-dextran, microprojectile bombardment, lipofection, whisker-mediated transformation, and other methods) depending on the type of cellular host.

In an embodiment of the invention, the rubidium chloride method is employed for the bacterial host, while the lithium-acetate method is used for the yeast host.

Transformation to specific regions of the yeast host genome may be accomplished by the flanking zeta sequences. In an embodiment of the invention, site-specific homologous recombination of flanking zeta sequence sites on the expression cassette with corresponding sites in the Ylt1+ yeast host cell genome is targeted.

In a further embodiment of the invention, non-homologous recombination of flanking zeta sequence sites on the expression cassette integrates at random targets of the Ylt1− yeast host cell genome.

The transformed bacterial host cell is cultured on a culture medium under conditions favouring growth of the cells for propagation of the vector. In an embodiment of the invention, the culture medium is selected from the group consisting of Luria-Bertani (LB) liquid medium and LB agar. In a preferred embodiment, LB agar plates supplemented with kanamycin are used, followed by inoculation into liquid LB media supplemented with kanamycin. The culture conditions, such as temperature, pH and the like, will be apparent to the ordinary skilled artisan.

Bacterial cells are typically harvested by centrifugation, disrupted by physical or chemical means and the resulting crude extract retained for further purification.

The expression construct, described herein, may be isolated and purified by a variety of processes as known in the art. Exemplary procedures suitable for such recovery and purification include salt-and-alcohol methods and silica-column purification. In a preferred embodiment, the Sambrook method (SAMBROOK, J.; MACCALLUM, P. and RUSSELL, D. Molecular Cloning: A Laboratory Manual. 3rd. Cold Spring Harbor Press, N Y, 2001. 2344 p. ISBN 0-87969-577-3) is used.

The transformed yeast host cell is cultured on a culture medium under conditions favouring the expression of the polypeptide. In an embodiment of the invention, the culture medium is selected from the group consisting of Yeast Extract Peptone Dextrose (YEPD) liquid medium and YEPD agar or the group consisting of Yeast Nitrogen Base (YNB) liquid medium and YNB agar. In a preferred embodiment, selective YNB medium is used. The culture conditions, such as temperature, pH and the like, will be apparent to the ordinary skilled artisan.

According to a third aspect thereof, the present invention provides for the use of expressed polypeptides secreted into the extracellular space by *Y. lipolytica* in biotechnological applications, the polypeptides including antigens.

The invention provides for the use of the foregoing polypeptides in biotechnological applications, including but not limited to vaccines, diagnostic kits or products, medicaments, antibiotic or antimicrobial formulations and nutritional additives.

In an embodiment of the invention, antigens for use in vaccine and diagnostic applications may be selected from among a range of candidates, including: beak and feather disease virus, Pigeon circovirus, *E. coli* pathotypes, *Avibacterium paragallinarum*, Newcastle disease virus, Infectious bronchitis virus, Infectious bursal disease virus, Chicken anaemia virus, Poultry Reovirus and *Lacctococcus garvieae*.

It should be understood that the design of the antigen for use as a vaccine component may depend on such factors as the size of polypeptide, the stability of the polypeptide, the degree of immunogenicity elicited by the polypeptide, the specificity of the immunogenic response elicited and the optimal codon sequence for a given host cell. The specific design of antigen for use in the above-mentioned candidates will be apparent to those skilled in the art.

In an embodiment of the invention, Psittacine Beak and Feather Disease Virus Coat Protein (BFDV CP) sequence of SEQ ID 5 is used to create components for a sub-unit vaccine against beak and feather disease virus. The vaccine may then be administered by methods including, but not limited to: intramuscular injection, addition of the vaccine components to food or drink or spraying.

In an embodiment of the invention, the foregoing polypeptides may be used to create components for a diagnostic kit. The diagnostic kit may be selected from a group including, but not limited to: rapid plate agglutination testing, direct Enzyme-Linked Immunosorbent Assay (ELISA), indirect ELISA, precipitation testing, complement fixation testing, neutralization testing and fluorescent antibody testing.

In an embodiment of the invention, the Psittacine BFDV CP sequence is used to create components for rapid plate agglutination tests and ELISA diagnostic kits against beak and feather disease virus antibodies in serum.

In an alternate embodiment of the invention, the Psittacine BFDV CP sequence is used to create components for a fluorescent antibody test and diagnostic kit against beak and feather virus disease antibodies in serum.

According to a sixth aspect thereof, the present invention provides for the use of polypeptides expressed as a fusion protein with a *Y. lipolytica* cell wall protein encoding element, the polypeptides including antigens.

The invention provides for the use of the foregoing polypeptides in biotechnological applications, including but not limited to vaccines, diagnostic kits or products, medicaments or antimicrobial formulations and nutritional additives.

In an embodiment of the invention, antigens for use in vaccine and diagnostic applications may be selected from among a range of candidates, including: beak and feather disease virus, Pigeon circovirus, *E. coli* pathotypes, *Avibacterium paragallinarum*, Newcastle disease virus, Infectious bronchitis virus, Infectious bursal disease virus, Chicken anaemia virus, Poultry Reovirus and *Lacctococcus garvieae*.

In a preferred embodiment of the invention, the Psittacine BFDV CP sequence is used to create a whole cell vaccine, inactivated cell vaccine or cell lysate vaccine and/or diagnostic kit components against beak and feather disease virus. The vaccine may then be administered by methods including, but not limited to: intramuscular injection, addition of the vaccine components to food or drink or spraying.

It should be understood that the design of the antigen for use as a vaccine component may depend such factors as the size of polypeptide, the stability of the polypeptide, the degree of immunogenicity elicited by the polypeptide, the specificity of the immunogenic response elicited and the optimal codon sequence for a given host cell. The specific design of antigen for use in the above-mentioned candidates will be apparent to those skilled in the art.

In an embodiment of the invention, the BFDV CP sequence is used to create whole-cell and inactivated yeast cell vaccines and diagnostic kit components against beak and feather disease virus. In a preferred embodiment of the invention, whole cells displaying Psittacine BFDV CP fusion sequences are used to create components for rapid plate agglutination and ELISA diagnostic kits against beak and feather disease virus antibodies in serum.

According to a seventh aspect thereof, there is provided a pharmaceutical preparation for use in the stimulation of immune response, comprising a therapeutically effective amount of at least one polypeptide, as identified herein, in combination with one or more pharmaceutically acceptable excipients, additives or carriers.

According to a eighth aspect thereof, there is provided the use of at least one polypeptide, as identified herein, in the manufacture of a medicament for the treatment, diagnosis and/or prevention of diseases and/or disorders.

The diseases and/or disorders referred to above may be selected from the group including, but not limited to: beak and feather disease, Young Bird Disease (YBD), *E. coli* pathotype infection, infectious coryza, Newcastle disease, infectious bronchitis, infectious bursal disease, chicken anaemia, Poultry Reovirus infection and lactococcosis.

These and other objects, features and advantages of the invention will become apparent to those skilled in the art following the detailed description of the invention as set out in the Examples.

Figure 1:
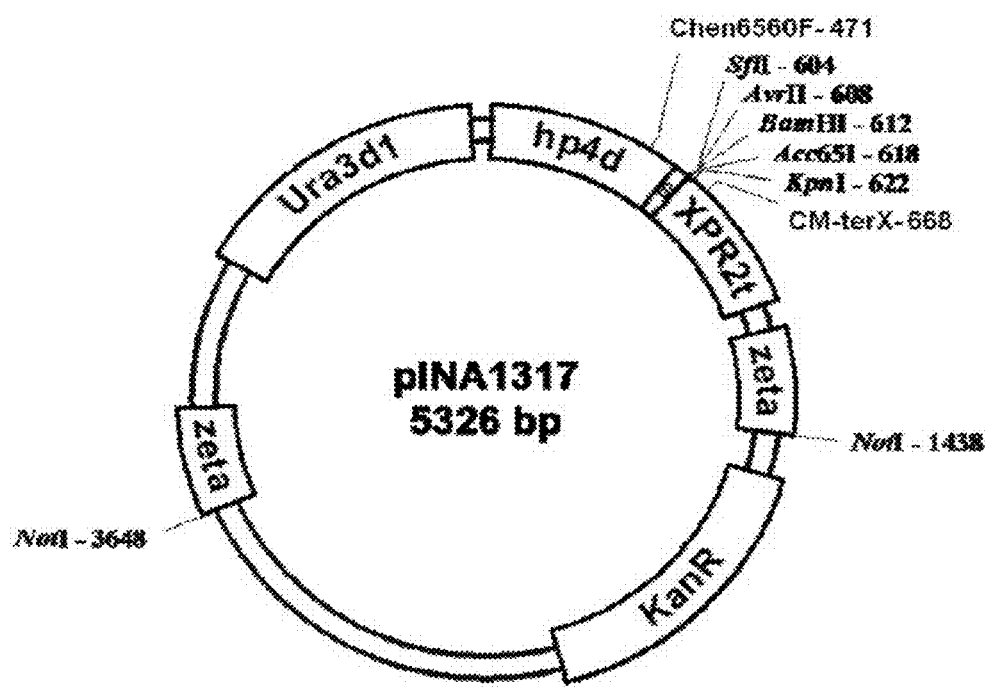
FIG. 1: Illustrates the important elements comprising the SECRETORY EXPRESSION VECTOR, where hp4d=promoter, S=secretion signal, XPR2t=terminator, zeta=integrative elements, KanR=antibiotic resistance marker for sub-cloning in *Escherichia coli*, and URA3d1=auxotrophic marker. Selected restriction endonuclease recognition sites and primer binding sites are also indicated.
Figure 2:
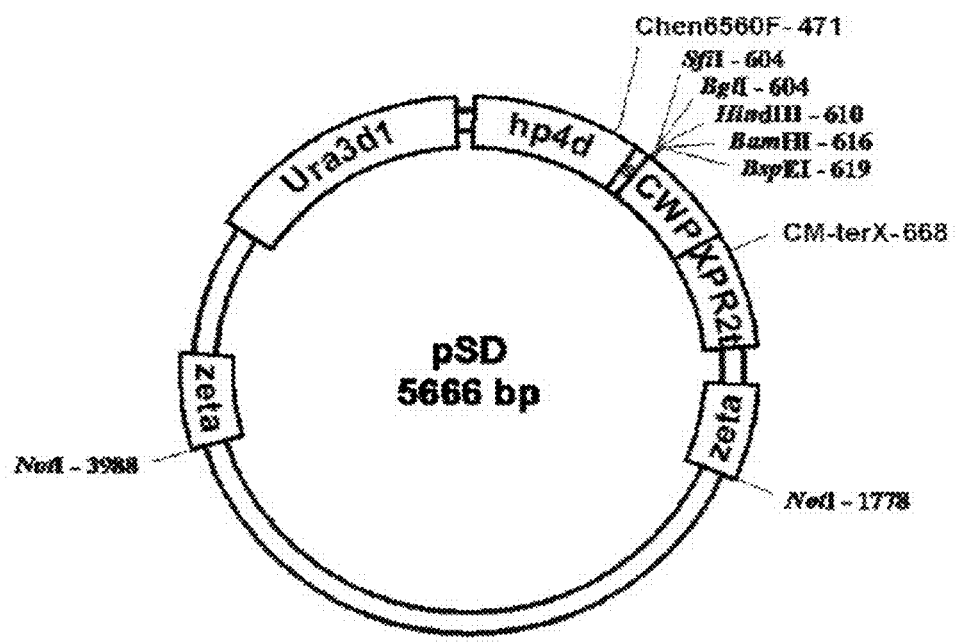
FIG. 2: Illustrates the important elements comprising the SURFACE DISPLAY EXPRESSION VECTOR, where hp4d=promoter, S=secretion signal, CWP=native *Yarrowia lipolytica* cell wall protein, XPR2t=terminator, zeta=integrative elements, KanR=antibiotic resistance marker for sub-cloning in *Escherichia coli*, and URA3d1=the auxotrophic marker. Selected restriction endonuclease recognition sites and primer binding sites are also indicated.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

EXAMPLES OF THE INVENTION

The invention was performed in accordance with the following steps.

Example 1 Production of Recombinant Psittacine Beak and Feather Disease Virus Coat Protein (BFDV CP) Using the *Yarrowia lipolytica* Expression System of the Present Invention Materials and Methods
Capsid Protein "Gene of Interest"

The gene encoding the BFDV CP was codon-optimized for expression in *Yarrowia lipolytica*, and synthesized by GeneArt. The initiation codon (CTG) and stop codon (TAA) were removed and SfiI (5') and HindIII (3') restriction endonuclease recognition sites were added to the sequence [AY450443—Beak and Feather disease virus isolate AFG3-ZA, complete genome]. The supplied lyophilised synthetic gene (5 µg plasmid DNA) was reconstituted in 50 µl 10 mM Tris-HCl (pH 8.0) upon arrival.

Strains and Media

*Escherichia coli* JM109 (endA1, recA1, gyrA96, thi, hsdR17 ($r_k^-$, $m_k^+$), relA1, supE44, Δ(lac-proAB), [F' traD36, proAB, laqI$^q$ZΔM15]) cells were used for plasmid manipulations and propagation. Standard molecular biology techniques were used as described in Sambrook and Russel (2001), unless explicitly stated otherwise. The *E. coli* transformants were grown at 37° C. in 5.0 ml Luria-Bertani (LB) broth [0.5% (w/v) yeast extract, 1% (w/v) sodium chloride and 1% (w/v) tryptone] supplemented with 30 µg/ml of kanamycin and on LB-agar plates supplemented with 1.5% w/v agar and 30 µg/ml of kanamycin.

The *Y. lipolytica* yeast strains used was Po1h (MatA, ura3-302, xpr2-322, axp1-2). The yeast strain was supplied by CBAI, AgroParisTech, 78850 Thiverval-Grignon, France. The yeast strain was grown in 50 ml of YPD [1% (w/v) yeast extract, 2% (w/v) peptone, 2% (w/v) glucose] medium in 250 ml flasks at 28-30° C. Yeast transformants were grown on YNB-N$_{5000}$ [0.17% (w/v) yeast nitrogen base without amino acids and ammonium sulphate, 1% (w/v) glucose and 0.5% (w/v) ammonium sulphate] or alternative Ura-selective medium [0.17% (w/v) yeast nitrogen base without amino acids and ammonium sulphate, 1% (w/v) glucose, 0.4% (w/v) ammonium chloride and 0.2% (w/v) CAS amino acids] plates at 28-30° C.

Other *Yarrowia lipolytica* strains besides Po1h that are included in this invention are Po1f (MatA, leu2-270, ura3-302, xpr2-322, axp-2); E129 (MatA, lys11-23, ura3-302, leu2-270, xpr2-322) and E150 (MatB, his-1, leu2-270, ura3-302, xpr2-322).

Plasmid/Expression Vector

The SURFACE DISPLAY EXPRESSION VECTOR is described as the plasmid pINA1317-YICWP110, while the SECRETORY EXPRESSION VECTOR is plasmid pINA1317 alone, i.e. without the gene encoding YICWP110. Both of these vectors contain the recombinant *Yarrowia lipolytica*-derived hp4d promoter to drive expression of genes of interest, and hence produce the corresponding protein of interest in a growth-phase-dependent manner. Due to the use of said hp4d promoter, the SECRETORY EXPRESSION VECTOR, the SURFACE DISPLAY EXPRESSION VECTOR, and derivatives of either vector that also contain said promoter, are protected by PCT/IB96/00562 to INRA and INA (presently AgroParisTech). This patent application protects the recombinant promoter, the vectors carrying it and the recombinant yeasts transformed with the said vectors.

The SECRETORY EXPRESSION VECTOR and the SURFACE DISPLAY EXPRESSION VECTOR use zeta sequences (Long Terminal Repeats of Ylt1 retrotransposon), which promote homologous (directed) integration of said vectors into the genome of Ylt1-containing *Yarrowia lipolytica* strains and non-homologous (random) integration of said vectors into the genome of Ylt1-devoid *Yarrowia lipolytica* strains. Due to the potential use of said zeta sequences for non-homologous integration, the SECRETORY EXPRESSION VECTOR, the SURFACE DISPLAY EXPRESSION VECTOR, and derivatives of either vector that also contain said zeta sequences are also protected by PCT/FR99/02079 to INRA and CNRS. This patent application protects the use of zeta sequences for promoting non-homologous integration into the genome of Ylt1-devoid *Yarrowia lipolytica* strains, and the recombinant yeasts obtained by such process.

Both the SECRETORY EXPRESSION VECTOR and the SURFACE DISPLAY EXPRESSION VECTOR contain the Ura3d1 marker for complementation of defective uracil auxotrophic markers present in receptive mutant strains. Variations of the vector have been constructed that contain the Leu2 marker for complementation of defective leucine auxotrophic markers present in receptive mutant strains, and are included in this invention. Furthermore, variations of the SECRETORY EXPRESSION VECTOR and the SURFACE DISPLAY EXPRESSION VECTOR which contain a promoter-deficient variation of the Ura marker, Ura3d4, which promotes multiple-copy integration into the genome of receptive strains, are also included in this invention.

Cloning of the Gene Encoding BFDV CP into the SECRETORY EXPRESSION VECTOR and the SURFACE DISPLAY EXPRESSION VECTOR For cloning of the BFDV CP gene into the SURFACE DISPLAY EXPRESSION VECTOR, endonuclease digestion of the vector containing the capsid gene (provided by GeneArt) as well as the SURFACE DISPLAY EXPRESSION VECTOR was performed, using SfiI and HindIII. The digestion reaction mixtures were electrophoresed on an agarose gel containing ethidium bromide. The appropriate sized bands were excised from the gel and purified using a gel band purification kit (GE Healthcare).

For cloning of the BFDV CP gene into the Secretion EXPRESSION VECTOR, the BFDV CP was amplified from the vector supplied by GeneArt using the primers BFDV SCF (5'-TCAAGGCCACGTGTCTTGTCC-3')(SEQ ID NO:7) and BFDV SCR (5'-TCCAGGTACCT TACTAG-GTGGGGTTGGGGTTG-3') (SEQ ID NO:8), using Kapa HiFi polymerase. The thermal cycling conditions included an initial denaturation step of 3 min at 95° C., followed by 25 cycles of denaturation at 98° C. for 20 sec, annealing at 60° C. for 15 sec, and extension at 72° C. for 1 min; followed by a final extension step at 72° for 1 min. The PCR products were also sequenced for authenticity verification.

The resultant PCR product (amplicon), referred to as BFDV CP PCR product, was electrophoresed on an agarose gel containing ethidium bromide. The amplicon was excised from the gel and purified using a gel band purification kit (GE Healthcare). The purified amplicon was then phosphorylated using polynucleotide kinase, and sub-cloned into pSMART by ligation. The PCR product contained a new stop codon (TAA) on the 3' end, followed by a KpnI recognition site.

Endonuclease digestion was performed on the pSMART vector containing the BFDV CP PCR product as well as on the SECRETORY EXPRESSION VECTOR using SfiI and KpnIII. The digestion reaction mixtures were electrophoresed on an agarose gel containing ethidium bromide. The appropriate sized bands were excised from the gel and purified using a gel band purification kit (GE Healthcare).

In both instances, purified BFDV insert DNA fragments were ligated to the appropriately prepared expression vector. Ligation mixtures were used to transform *Escherichia coli* JM109 cells that had been made competent using rubidium chloride, and transformed cells were streaked out on LB plates supplemented with kanamycin. Single colonies that formed on the LB-kanamycin plates were used to inoculate test tubes containing 5 ml LB broth supplemented with kanamycin, and the tubes were incubated at 37° C. for 16 hours.

Plasmids were isolated from the inoculated cultures using the lysis by a boiling method for mini-preparation of plasmid DNA, or by using the QIAamp DNA mini kit (Qiagen). The presence of the inserted gene of interest in the expression vectors was confirmed by restriction analysis or PCR on isolated plasmids.

Prior to transformation of *Yarrowia lipolytica*, the isolated recombinant plasmids were digested with NotI, to separate the yeast-integrative cassettes from the bacterial moieties of the vectors, resulting in yeast-integrative cassette devoid of a bacterial genetic material. The yeast-integrative cassette was separated from the bacterial backbone by agarose gel electrophoresis, followed by excision from the gel and purification gel band purification kit (GE Healthcare).

Figure 4:
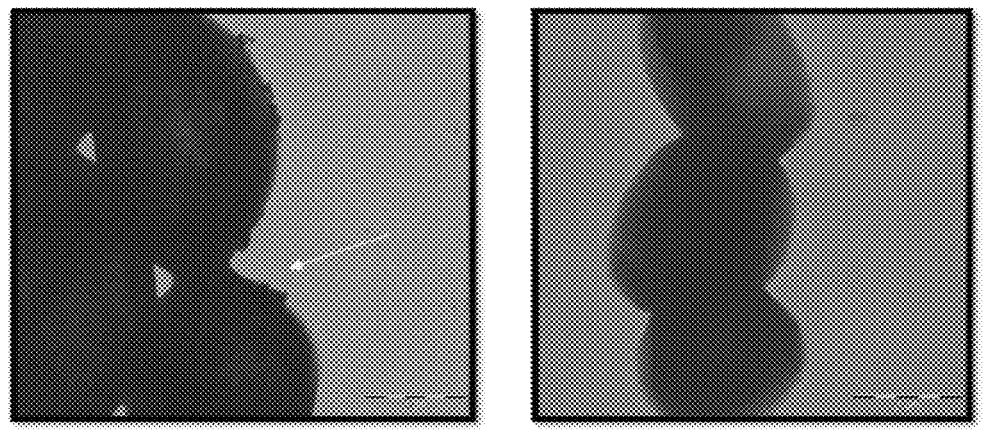
FIG. 4: Immunofluorescence of (A) transformed *Y. lipolytica* and (B) untransformed *Y. lipolytica* reacting with FITC-linked antibodies. (C) Immunofluorescence image of positive reaction superimposed on light micrograph, which demonstrates the location of fluorescence predominantly on the cellular surfaces.

*Yarrowia lipolytica* strains were transformed using the purified yeast-integrative cassettes according to the methods of Madzak et al. (2005) or Chen et al. (1997). Recipient *Yarrowia lipolytica* strains were also transformed with the 'empty' expression vectors, i.e. expression vectors into which no gene was inserted. Transformants (as shown in FIG. 4) from these transformations would serve as negative controls for the transformants into which the BFDV CP gene was integrated. The transformation mixtures were streaked on YNB-based selective medium, and incubated at 28-30° C. until transformant colonies were observed. Yeast transformants were selected from the selective medium plates, and re-streaked on selective medium for three passages to improve stability.

Total genomic DNA (gDNA) was extracted from *Yarrowia lipolytica* transfromants using the method described by Albertyn and Labuschagne (2007). Isolated transformant gDNA samples were used as templates for PCR confirmation of the integration of the BFDV CP gene. This was done using the primers: Chen6560F (GATCCGGCATGCACT-GATC) (SEQ ID NO:9) and CM-terX (GAACCTCGTCAT-TGATGGAC) (SEQ ID NO:10). The forward primer Chen6560F was designed based on the XPR2 promoter region of the vectors, while the reverse primer CM-terX was designed based on the terminator region of the plasmid.

The primer combination therefore amplifies the MCS and parts of the surrounding regions. In the absence of an insert, these primers result in amplicons that are 235 base pairs (bp) in length for the SECRETORY EXPRESSION VECTOR and 575 bp in length for the SURFACE DISPLAY EXPRESSION VECTOR. The difference in length is due to the presence of the GPI-anchored YlCWP in the SURFACE DISPLAY EXPRESSION VECTOR. In the presence of the BFDV CP gene within the expression cassette, the primer combination results in amplicons that are 974 bp in length for the SECRETORY EXPRESSION VECTOR and 1316 bp in length for the SURFACE DISPLAY EXPRESSION VECTOR.

The thermal cycling conditions included an initial denaturation step of 2 min at 95° C., followed by 30 cycles of denaturation at 95° C. for 30 sec, annealing at 55° C. for 1 min and extension at 70° C. for 1.30 min; followed by a final extension step at 70° for 5 min. PCR amplifications were also performed using Ready-to-go PCR Beads (GE Healthcare). The resultant amplicons were also sequenced for authenticity verification.

Once transformants had been confirmed to have integrated the cassette, glycerol (15% v/v) was added to culture aliquots, followed by cryopreservation at −80° C. Transformants were revived by streaking from the frozen stocks onto selective YNB-based agar plates, which were incubated at 28-30° C. Pre-cultures of 5 ml YPD were inoculated from the plates, followed by incubation for 16 h on a rotary shaker at 28-30° C. at 160 rpm. The 16 h pre-cultures were used as inoculums for main cultures of 45 ml YPD (hence 1/10 dilution). Main cultures were incubated for 48 h on a rotary shaker at 28-30° C. at 160 rpm.

Cells were harvested by centrifugation at 7000 rcf for 10 min, separating the cells (pellet) from the surrounding medium (supernatant). When using the SURFACE DISPLAY EXPRESSION VECTOR, the cell pellet is washed and resuspended in PBS (5.84 g sodium chloride (NaCl), 4.72 disodium hydrogen phosphate ($Na_2HPO_4$) and 2.64 g sodium dihydrogen phosphate ($NaH_2PO_4$), pH 7.2), while the supernatant is discarded. When using the SECRETORY EXPRESSION VECTOR, the supernatant is collected for further use while the cellular pellet may be discarded.

Preliminary Tests of Applications

Rapid Plate Agglutination Test for the Detection of Antibodies

Figure 3:
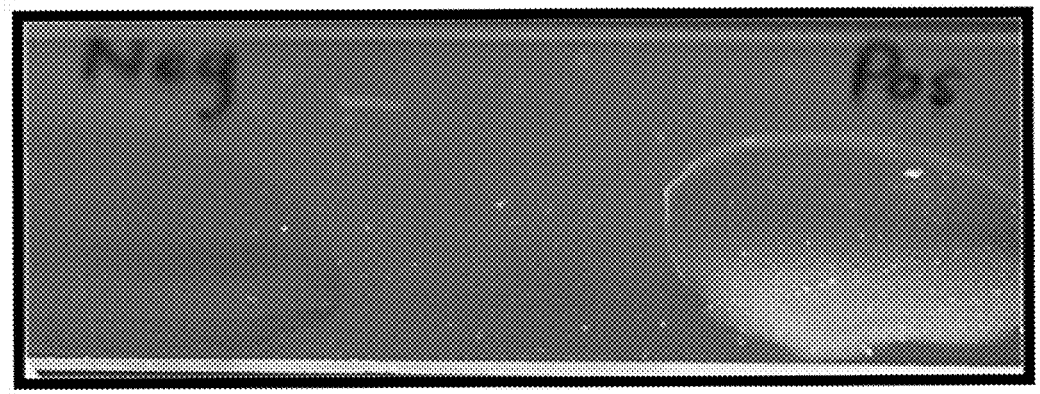
FIG. 3: Illustrates the results obtained with the rapid plate agglutination test for the detection of Beak and Feather disease virus antibodies. Visual Agglutination reactions were observed with Pos) Test: Expressing yeast cells mixed with known positive BFDV antibodies, compared to Neg) Negative control: non expressing yeast cells mixed with known positive BFDV antibodies.
Figure 3:
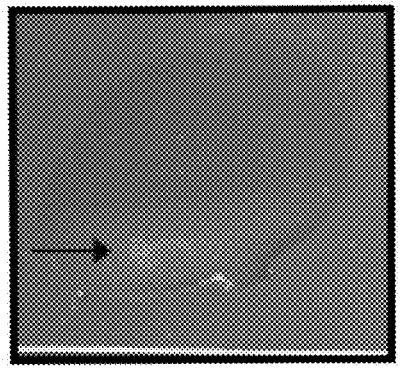

For rapid plate agglutination the SURFACE DISPLAY EXPRESSION VECTOR was used. Yeast transformants were harvested by centrifugation at 7000 rcf for 10 min, separating the cells (pellet) from the surrounding medium (supernatant). The cell pellet was washed and resuspended in PBS (5.84 g sodium chloride (NaCl), 4.72 disodium hydrogen phosphate ($Na_2HPO_4$) and 2.64 g sodium dihydrogen phosphate ($NaH_2PO_4$), pH 7.2). All reagents were allowed to come to room temperature, so as to eliminate the possibility of non-specific reactions. A drop of the antigen (yeast transformant culture) (10 µl) was placed on a clean microscope slide, after which 10 µl of serum was added. The slide was rotated for 30 seconds and the presence or absence of agglutination was noted. A serum sample was considered positive when clear agglutination was observed, as easily visible clumps, whereas the absence of agglutination was interpreted as negative (FIG. 3). All reactions were run in parallel with negative controls that consisted of non-BFDV CP-expressing cells (non-expressing yeast cells, transformed with empty plasmids).

Immunofluorescence

Aliquots (20 µl) of yeast transformants were dropped onto cleaned microscope slides and the yeast cells were heat-fixed onto the slides. This was followed by a 15 min blocking step at room temperature (RT) using 20 µl of a solution of 5% skim milk in PBS-Tween. The slides were washed using PBS-Tween, before addition of specific mouse-raised monoclonal antibodies (GenScript), diluted 1:100 in PBS (starting concentration 4.51 mg/ml). The slide was incubated for 1 h at RT. The slides were washed using PBS-Tween, before addition of Fluorochrome-conjugated secondary antibody (FITC) conjugated, anti-mouse IgG (whole molecule, Sigma), diluted 1:1000 in PBS; and further incubation for 1 h at RT in the dark. The slides were washed using PBS-Tween. The slides were immediately viewed using a fluorescence cell imager (ZOE™ Fluorescent cell imager, Bio-Rad laboratories) at an excitation of 480 nm and emission of 517 nm, using the green channel.

The invention claimed is:

1. A genetic construct for inducing expression of a polypeptide in *Yarrowia lipolytica* (*Y. lipolytica*), the construct comprising an expression cassette comprising an acid extracellular protease secretion signal sequence, flanking zeta sequence recombination sites, at least one promoter element, at least one polypeptide encoding region and at least one terminator element;
wherein the at least one promoter drives expression of the at least one polypeptide encopding region;
wherein the polypeptide encoded by the at least one polypeptide encoding region is SEQ ID NO: 6 and the polypeptide encoding region is SEQ ID NO: 5;
wherein the polypeptide encoding region of SEQ ID NO: 5 is a sequence that has been codon-optimized for expression in *Y. lipolytica*; and wherein the expressed polypeptide of SEQ ID NO: 6 maintains its immunogenicity.

2. The genetic construct of claim 1, wherein the extracellular protease secretion signal sequence comprises the nucleotide sequence of SEQ ID NO: 1 and the flanking zeta sequence recombination sites comprise the nucleotide sequence of SEQ ID NO: 2.

3. The genetic construct of claim 1, wherein the construct is in the form of a plasmid.

4. The genetic construct of claim 1, wherein the construct comprises a *Y. lipolytica* cell wall protein encoding element, located between the polypeptide encoding region and the terminator element.

5. The genetic construct of claim 1, wherein the genetic construct comprises a Multiple Cloning Site (MCS) located between the acid extracellular protease secretion signal sequence and the terminator element of the expression cassette.

6. The genetic construct of claim 5, wherein the genetic construct comprises a *Y. lipolytica* cell wall protein encoding element located between the MCS and the terminator element.

7. The genetic construct of claim 4, wherein the cell wall protein encoding element comprises the nucleotide sequence of SEQ ID NO: 3, or a fragment thereof.

8. The genetic construct of claim 1, wherein the acid extracellular protease secretion signal sequence is located between the promoter element and the polypeptide encoding region.

9. The genetic construct of claim 1, wherein the acid extracellular protease secretion signal sequence is located between the promoter element and a Multiple Cloning Site (MCS).

10. The genetic construct of claim 1, wherein the promoter element comprises the nucleotide sequence of SEQ ID NO: 4.

11. The genetic construct of claim 1, wherein the construct comprises one or more auxotrophic marker regions for the purposes of replication and selection in yeast host cells.

12. The genetic construct of claim 1, wherein the genetic construct comprises one or more bacterial moiety regions for the purposes of replication and selection in bacterial host cells.

13. A method of transforming a *Y. lipolytica* host cell with a genetic construct or a combination of genetic constructs as claimed in claim 1, the method including the steps of:
transforming the expression cassette or cassettes into a *Y. lipolytica* yeast cell;
isolating the transformed *Y. lipolytica* yeast cell; and
culturing the transformed *Y. lipolytica* yeast host cell so as to express one or more polypeptides into the extracellular space or onto the host cell wall.

14. The method of claim 13, wherein the *Y. lipolytica* host cell is selected from the group consisting of: Po1h (MatA, ura3-302, xpr2-322, axp1-2); Po1f (MatA, leu2-270, ura3-302, xpr2-322, axp-2); E129 (MatA, lys11-23, ura3-302, leu2-270, xpr2-322) and E150 (MatB, his-1, leu2-270, ura3-302, xpr2-322).

15. A non-yeast host cell comprising a genetic construct as claimed in claim 1.

16. A *Y. lipolytica* host cell comprising a genetic construct as claimed in claim 1.

17. A method of producing a polypeptide wherein said method comprises transforming a host cell with a genetic construct of claim 1, and expressing said polypeptide from said transformed host cell.

* * * * *

SEQUENCE LISTING

```
<160> NUMBER OF SEQ ID NOS: 10

<210> SEQ ID NO 1
<211> LENGTH: 45
<212> TYPE: DNA
<213> ORGANISM: Artificial Sequence
<220> FEATURE:
<223> OTHER INFORMATION: XPR2 acid extracellular protease sequence

<400> SEQUENCE: 1
atgaagctcg ctaccgcctt tactattctc acggccgttc tggcc            45

<210> SEQ ID NO 2
<211> LENGTH: 714
<212> TYPE: DNA
<213> ORGANISM: Yarrowia lipolytica

<400> SEQUENCE: 2
tgtaacactc gctctggaga gttagtcatc cgacagggta actctaatct cccaacacct     60
tattaactct gcgtaactgt aactcttctt gccacgtcga tcttactcaa ttttcctgct    120
catcatctgc tggattgttg tctatcgtct ggctctaata catttattgt ttattgccca    180
aacaactttc attgcacgta agtgaattgt tttataacag cgttcgccaa ttgctgcgcc    240
atcgtcgtcc ggctgtccta ccgttagggg tagtgtgtct cacactaccg aggttactag    300
agttgggaaa gcgatactgc ctcggacaca ccacctgggt cttacgactg cagagagaat    360
cggcgttacc tctctcacaa agcccttcag taccgccgcc tgtcgggaat cgcgttcagg    420
tggaacagga ccacctccct tgcacttctt ggtatatcag tataggctga tgtattcata    480
gtggggtttt tcataataaa tttactaacg gcaggcaaca ttcactcggc ttaaacgcaa    540
aacggaccgt cttgatatct tctgacgcat tgaccaccga gaaatagtgt tagttaccgg    600
gtgagttatt gttcttctac acaggcgacg cccatcgtct agagttgatg tactaactca    660
gatttcacta cctaccctat ccctggtacg cacaaagcac tttattttct caca          714

<210> SEQ ID NO 3
<211> LENGTH: 666
<212> TYPE: DNA
<213> ORGANISM: Yarrowia lipolytica
```

<400> SEQUENCE: 3

```
atgaagttca ccgccgccac cctccttctc gccgccgccg cctctgctct tgacgttgtc    60
accgacggct ccaagccctt tggcatcatg tctctgcgat ccgcctccgc catccacctc   120
tcctcggtag gcgtctccgg tgacgctctg accattggc cttccggcgc caagttcacc    180
atcaaggacg gcgtcctcta cgccgacgac aaggccattg acttctcctc cggcgaggcc   240
aaggtcgctt ccgacggcaa gggtacctcc ggcgtcaccc tcgagaaggg ctacgtgacc   300
gtccccggct taactgggc cggctgcccc gagggcaacg gttacgccgt cgacgacaac    360
tccaagtgcg aggacgacgg aatccccttc ggcgcctacg ctgttgctga cacctccgca   420
gagtcttctg ccgccccgc ctcttctgcc gccgctgccg agtcctctgc cgcccccctct   480
tccgctgctg aggccaagcc caccgctgga ggtaacaccg gcgccgtcgt cacccagatc   540
ggtgacggcc agatccaggc tccccctct gctcctcccg ctgcccccga gcaggccaac    600
ggcgccgtct ctgtcggtgt ttctgccgcc gctctcggtg tcgctgccgc cgctctcctc   660
atttaa                                                              666
```

<210> SEQ ID NO 4
<211> LENGTH: 9453
<212> TYPE: DNA
<213> ORGANISM: Artificial Sequence
<220> FEATURE:
<223> OTHER INFORMATION: Recombinant hp4d promoter element

<400> SEQUENCE: 4

```
tgtaacactc gctctggaga gttagtcatc cgacagggta actctaatct cccaacacct    60
tattaactct gcgtaactgt aactcttctt gccacgtcga tcttactcaa ttttcctgct   120
catcatctgc tggattgttg tctatcgtct ggctctaata catttattgt ttattgccca   180
aacaactttc attgcacgta agtgaattgt tttataacag cgttcgccaa ttgctgcgcc   240
atcgtcgtcc ggctgtccta ccgttagggg tagtgtgtct cacactaccg aggttactag   300
agttgggaaa gcgatactgc ctcggacaca ccacctgggt cttacgactg cagagagaat   360
cggcgttacc tctctcacaa agcccttcag taccgccgcc tgtcgggaat cgcgttcagg   420
tggaacagga ccacctccct tgcacttctt ggtatatcag tataggctga tgtattcata   480
gtggggtttt tcataataaa tttactaacg gcaggcaaca ttcactcggc ttaaacgcaa   540
aacggaccgt cttgatatct tctgacgcat tgaccaccga gaaatagtgt tagttaccgg   600
gtgagttatt gttcttctac acaggcgacg cccatcgtct agagttgatg tactaactca   660
gatttcacta cctaccctat ccctggtacg cacaaagcac tttattttct cacatctggt   720
ggacgacacc tcgttttttgt ttcgagtgat agcctgccag atttattgtg cctttactgt   780
cgtaccagcg tattttactt cccttttccgt tctttcgttt tcaccatgtc gaaagtaaca   840
aaagacgagt tccaggctct caccgcgaag atggacgcct tgacgctctc ccaccaggag   900
atcaccacta ctctcgctac cgcggttaat accaaggaat tccgctcagc cttagacgag   960
ctcaagcagt caaatgagtc tttcaagaca catcaggctg gggagtttga aaagttgcac  1020
cagttggtgt cggcccagca cgaaaccatc gcgaacctca gcaagcgtgt cgactcaccc  1080
ccgagcacca gctcccttga aggcatttcc cgtattggca aggctgattc cgaatttgaa  1140
cccgacaccc cccagaaggg taactctgtc ctacatggca tggactttgc tgccagtgac  1200
acgggttctg ttgactatcg aaaagaatcc gacgccctca agtccatcat ccggaacgag  1260
```

-continued

| | |
|---|---|
| gtttacccct ccttgtccag cgaagaattc cgaaaacagt tgtacgctta caaatctttt | 1320 |
| gattcccggg tggctacctt tatcctactc caggatgaca tccgttggag caccagagct | 1380 |
| cgggctttcc acctttggtg cggtgtcaac gataagcagc ccctcttcga tcaacagtac | 1440 |
| ctccaactcc gaagcacctt tgaagcgag actgctgatg aatcaaccaa gccaggtgcc | 1500 |
| cacgctcgtc tgaacaccgc ttgcgaacgt ctcctccggg accttttcg aaagcgcggg | 1560 |
| tttgaccacg aacctgctgt ctcctttgct gaacaagagg aggaactccg tttccggttc | 1620 |
| aaagattacc acaccgcttt ctctatcgag acactacgtg cgtacctctc tgctctgagc | 1680 |
| accgctctga cctcctcacc tctgccggtt ctctctcggt gtctccagtt gcagaagctc | 1740 |
| gctccgactc acctgggcac cgccctcgga cgcgagatcc ctcgtgacaa cactcgttgg | 1800 |
| ctgagccttg gcatggactc cgaccctgag cgtgaccatc aagttgccac ggagctcatc | 1860 |
| cagcccctcg ccaagatgat cacccaacat gtccaacgac ttgacgatct caatgatgag | 1920 |
| gctcttctga gatggcgaca gcacacggta tctttcgaag acgtgtggat gtgggtcgag | 1980 |
| ccttccgccc cacctgagcc ttccacgcct gaacctgaca aagtcgtcgt tcacgttgcg | 2040 |
| ggacgtggtc gttccaccag gaagcctgcc gacggccctg tctcaactga gactgtgcag | 2100 |
| aaacccacaa tccgtgcctc ggatgcctca acctcctggg cagctgacaa ggctccttgt | 2160 |
| gttttctgtg gttccactgc ccatgcactg gtcaactgcg atgactccga aggcagcccc | 2220 |
| ttggtcaagg ccaagtacct tggcagcttc aagtctttca cccgacttgg ctaccagggt | 2280 |
| tttgaaaagt atctatcgcc tgttgatgct gacttccctc taaaacagag cgctctctac | 2340 |
| acttcctgga agcagaagga atggtcgaat ccgcttatgg agcctagact tcgaacttcc | 2400 |
| aatgcgcagt ggcgtcctgc cctagctggc cgcgtaaatg ccgttgaatt tgtacacgtt | 2460 |
| gaagacccag gcgggccttt ggataacagc tatgactctg actcatctgc gtctggttat | 2520 |
| gacttccagg accttctcca acccggcacg ttcagtgtct gtctaggagg ggtgcctcga | 2580 |
| gatcttctgt ctgatacgtt ttcctcctac gacgagcctc gcactatcat tgactccact | 2640 |
| gactcccagc ttgagctcac gaaagaggca atccaccagc acattctcca gatggcaaaa | 2700 |
| cagcccacac ccctccccgt cacttacgca attgatgcgc ctgtgtcagg ctcctacagt | 2760 |
| ggcaacatga agcgccttgt ggcacaccca gccttcatgc agctcgtagc tcgcttaact | 2820 |
| gctccccgg gcacgttcaa agcctccacg cttgaagcgg gttttgtagg tgctgttatg | 2880 |
| gccccgtctt ccccagttgc cggccgtgtc tactttgttg atgcggtcca gcgattgctc | 2940 |
| aacaagtaca acgtagtatt gcctacgaag ctttacgagt gtttcgctac agtccgaaat | 3000 |
| gacctcatgg agcccgctta cgccaccgaa ggcgatcctc gccgacagtc tctcaagacc | 3060 |
| aacatcaacg ccttgaaaac tgttgtcgac agcaagcacc ctgacagacc agtggctccg | 3120 |
| ttgccgcgac gcagcccccg tcgtgatgtc cgtgaagaca tgccccgcc tgctttgcct | 3180 |
| caagcgacaa aacgtggtgc cgcttcttct acggtatctt ccgctgctcc ccccactgct | 3240 |
| aagcgaacca aggctgtagc caatccctcc tcagtgggc cgactgactc cgcatcctcc | 3300 |
| acgggcgctg ttgttgacgt ccccagctct cgtgtggctg ttcaccccc ccgtctgggt | 3360 |
| gataaccact acgtgagccc tggaacccgt gtcaccaacc acatccacga tgcctctgcc | 3420 |
| gttgcggaga atgcacccct taaaagattac aaggatgctc tggaccgcct cccgtctgac | 3480 |
| ctagaggact ccaaggctct cttcaccaga gatcatcctc gttacgacaa tgccttgctg | 3540 |
| aaggctgggc gtctccctct cttcaagctt gaggccattc atgctctgcc ggaatcggaa | 3600 |
| aaagcagact tgtttgagcg catcctcaag gcgtcggatg ttgatggcct cgttctttt | 3660 |

```
gagcttctcc aggtgtgccc tgacctcaca aagtacattt ggaagaactt ccgtcaccag    3720
cggcaccggc ttgcgggtcc tgacatccaa gccatcgctc ttgagctcgg ggacgatctc    3780
atggagtgtg ccatggatct tgcgctcaac gtgatttcgt ccacaccgta tgagctcaac    3840
tctggcacct tcggtcgtct tcaggaggtt ttcaccacca ttgaccgtca gctgtacgac    3900
gacaaagttg gtaggccact ctcgccccac ttcaccgaca acattgctct tttcgaccaa    3960
cagaccagcg cccttttga cagtggctcg tctaacaacg tcatcgacac tgatttcttt    4020
gcccttgtac tcgcgaaggc tggtgtcacc cctgaccggg tgattgtttt ttctgacgga    4080
cagtcccacg ccacagtcgc aaacggagcc aaggtaaaag ttgatttctg ggcgcttctc    4140
cctgtcactt tcctgggtgt cgttactctt gaaacatttt gtgtcatgaa gtgcagcatg    4200
aagtgtattc tcggcaccgg atacatcagc aaactgcgca tttcgttcga ccatgatcgt    4260
taccgtgtcg cttcagtgga gaaccctggt aaccctggcg tccggtgcta ccctagtgac    4320
agaccttcag ctggccttgt tgctcacctt ggggttgctg accgtcttgt gaggcccggc    4380
cgccggcctg tgcctgcgtt tcctgctgcc aagctgtctc gccaaaacgt catggcacac    4440
gttcgaccca ctccctcact ctgtggtgat gttgatgaag caacaaatct ccttgacgcc    4500
tcatctctcg gagggcctca gcctggatct tactcccacc gttctgaaac agcggcaggc    4560
tgttttgcca tatcctttgc tgatgactgt gagtctgccg gccgccttc gagcgctgcc    4620 accgccattc tcaaggctct agcgtccagc tccggccctg atccccttgg cattccccct    4680
cgtgatgacc ctgacgagtc ttactcctca tcacctgggc accacggtga tgtctctggc    4740
gagcccaact cctcatcacc tgggcacacc tccgctcccg tcgacggtac gcttggacct    4800
ttactgccta ccgatgcctc atctgtggat gactccaacg agctctgctc ctcctcttca    4860
ggctcggaag ccccgtcgga agcccgtcc ggagtctcgg ccgccttgtc agatgtaggc    4920
accgttttcc aggagagcta cacgtcgtac cgtttccatg acaacttgc agacaatgct    4980 cttcatgcca gacccccga cgctcatgct ctcagtggtt ttatttcttc tgccgacctc    5040
gacagtgttt tccagtatcc acctcctgca tcgccctgca gctgctgcca gcagcctgta    5100
cgtgagtgtc gtgtacttgg taacactgtt ttcatcatgg ctgacattgg cgactcggct    5160
accatcgttc aggttcaacc ggatactgac ctgtccatgc gccaacagct ctaccttgct    5220
gaagttctca gtgatgccca agaaatcacc cctgaagact ctctgcattc tttatctgtc    5280
tccgtcaatg ccatgtacaa gccgctacac aagcgttctc tgcctctaaa taagcttcgc    5340
ccggacggtt cctttcctgt cggtgacggc tccaagcctt ctccgcgaca tcgcaacttc    5400
tctggcgacg agtcttgcca atttgatgcc aaacttgctc cagtccttt cccggccgag    5460 cttgctctct gtcgccatcg catgtcggac acggagggtg tctgggcttt caacgaagac    5520
caggagggtg tcctcagtca ccatattgag gagcccacca agatctacgt ggaagaggga    5580
ggcgttatca actcaaagca cttccctctc cgcggggcta tggtcggcgc tgccaaagac    5640
atcatcatga agggtctcgc caacggccag atggagccca gctcctcccc ccaccgcaac    5700
gcctggttcc tcgtgagcaa aaagagctcg ggataccgtt tcatccttga ctgccagggc    5760
ctcaacaaga tcaccttgag agatgctttc cacccaccca cgcggacct cctggctgag    5820 agtttctgtg gtcgtgctgt aacttccctg cttgacatta agaatggtta cggtcagaag    5880
gagattgctc ccgagtcccg tgacttgacg gcttttaaca cagattttgg ctcctatcgg    5940
ttaacgcgcc tgcctcaagg ttggtgcaac tctccagcgg tgttccaccg tgccatgctg    6000
```

```
cgcgtacttg ggccctctt tccggatcag gctgttgttt tcttggacga tattggcgtt   6060
ctcgggccta agactgacta tggcggagcc atgcatgacg actttccggg ctgccgccgg   6120
tacatcgtcg aacacatgga caacctcatg gctgtgcttc agaatctcta tgaagcgggt   6180
ctgactgtgt ctttcgacaa ggccgagctt ttcgtcagtg aggctgagtt cctcggtttc   6240
ctcactacct ctgaaggccg cttcccgtcc cctggcagtt ccgagaagat cgaatctttc   6300
gagttcccca ctactgtccg tggtgtgcgc tcttttctcg gtgctgtggt gtattttcgc   6360
atgtggatcc ctcatttcag cagtatcgct gcacctctgt acgactgcat ctccgctgcg   6420
cagaaggctg gcaaactcaa gatcaccaag accgaggcca ccgagtctgc ttttatggcg   6480
ctaaaaaagg ctatggtgag ccctgcggtt ctgcaccgct acgacccac cttacctatt   6540 gtcatcacca ctgatgcgtc ctccctcgga tggggcgcag taatgtctca catcgtcagt   6600
gttggccctc cggctgcccg tcgccccgtc cgtttcgaga gtggtttgtg gaaccccact   6660
gagcgtacct acgcatccac caagactgag tgccttgctg taaaacgtgc cttggagaag   6720
tgccgtcact atgtcactgg cgttcatttc gtgatcgaaa ctgacaacca ggccctggtt   6780
ttcctactgc agcaatcccg agttgaactc cctaacgcta tgttcacccg gtggtttgct   6840
tacatcaaac agtttgatta cgaggttcga tttgttaaag gccgagacaa tccagtggcc   6900
gattggctga gtcgtgagaa attttctgac ttccgacctg tcgattttcg ccctcctgtt   6960
gctgatacag ctcgacaagc tgatgagctt gctccgcttg tgccccgac ttggtcccct   7020 gtggcctcca tcactgtcct gtccattggt ccagagcccg ttttcatcca caaaggcatc   7080
tctctcgatc tcattttcac caccattgcc tccggcgatc ttgatcgaga tggtgttgac   7140
attccgccta gactgcgtca aatctgctct gagttcttca ttttgacga cattctccta   7200 ctgatcagct cacctggtct ccatcgacgt gttctcttca cagagaagga ggtgtctgag   7260
gttctccgag ctacccatga acaatatggc caccgcggtg ctgctgccat ccttcatgct   7320
ctccgtcgcc tctattactg gccgggcatg gctgatcacg tgaagtccca tcgtgcatca   7380
tgcggcacgt gtgcaaaagc caccaaccat ggtcttctca aggcgagtct ccacttcgtg   7440
gttccccgtc tcatttggga gacagtccag ctggacatcc tctaccttcc cgctgttcat   7500
ggtcccacca aggagtaccc cgatctggct gatcccgcca aggctctcgc tgctcaaacc   7560
accctcaccg acttcctccc cactgcccct cagttcactg atgtttcctc tgcccccgc   7620 ggacggctaa atgtcactat tgcccctac cagtatgtcc ttgtcgctcg tgatgaattc   7680
tctggctggc ctgaggcggt gccccttacga agtatcaact ctctctccac agccgctttc   7740
ttctacgatt tcatcattgc tcgttttggc gttccccgtc gggtctacac tgacggtggt   7800
agtgagttca agggtgattt taagcatctc tgcgaagatt tccacatcaa gcaggttttc   7860
accactcctg ctcatggtca atcgactggc attgtggaac gcggtcacca aaacctcctc   7920
cactgcctgc gcaaatacgg tcgtcagtgg atcttatacc tccacaccgc cctctgggct   7980
gaccggtgca cccgtcgttc atccacgggt aagtcacctt ttgagctgat gtatggtgtc   8040
tctggtgtct tgcctgtcga aagtcgtttc ctgacctgga attacctcag tggcaagacc   8100
gacctggccc acaacgaccc cgctcatgct gcttttctgc gcaccttgca acttgctgct   8160
tctactttcg aagttggctc tgctcgtgac cacctgaccc tgcaacgcca gcgtcaaaag   8220
gcgttctacg acaaacatca caacacagct gatacagatc ccttggccgt aaatgatttc   8280 gttttttgttc acgacctccg tccccacaac aagctgactc ctcgttggac tggtccctcc   8340
atcgtgaccg cgtgtcaccc tgagaccagc acgtacactg tcaacgatgt tgacggtgag   8400
```

```
aacccgcggc gtatccaccg caaccgcctc aaggttttcc accccgcttc catcgttgag    8460
ttccaggacc gcatgaagga acatcagtcc cgcgagtctg ctctccctgc cattcctggc    8520
cgcttttctg cctgttctcc acatgttctt ccccggctt cagtggctac tcgttccgtc     8580
cgttctgcag ctaccactgc gtcgactaga gttacttctc ggtcgaagct cgctcgtgtt    8640
gattctgggc ttgctcaggg ctccttcctt gctcagggcc tttattcttg attcttctaa    8700
ccagggcttc gggacgaaac cccgttagac ctgggcaggt gtaacactcg ctctggagag    8760
ttagtcatcc gacagggtaa ctctaatctc ccaacacctt attaactctg cgtaactgta    8820
actcttcttg ccacgtcgat cttactcaat tttcctgctc atcatctgct ggattgttgt    8880
ctatcgtctg gctctaatac atttattgtt tattgcccaa acaactttca ttgcacgtaa    8940
gtgaattgtt ttataacagc gttcgccaat tgctgcgcca tcgtcgtccg gctgtcctac    9000
cgttaggggt agtgtgtctc acactaccga ggttactaga gttgggaaag cgatactgcc    9060
tcggacacac cacctgggtc ttacgactgc agagagaatc ggcgttacct ctctcacaaa    9120
gcccttcagt accgccgcct gtcgggaatc gcgttcaggt ggaacaggac cacctccctt    9180
gcacttcttg gtatatcagt ataggctgat gtattcatag tggggttttt cataataaat    9240
ttactaacgg caggcaacat tcactcggct taaacgcaaa acggaccgtc ttgatatctt    9300
ctgacgcatt gaccaccgag aaatagtgtt agttaccggg tgagttattg ttcttctaca    9360
caggcgacgc ccatcgtcta gagttgatgt actaactcag atttcactac ctaccctatc    9420
cctggtacgc acaaagcact ttattttctc aca                                 9453

<210> SEQ ID NO 5
<211> LENGTH: 750
<212> TYPE: DNA
<213> ORGANISM: Psittacine Beak and Feather Disease Virus

<400> SEQUENCE: 5
ctgtggggca cctctaactg cgcatgcgct atatttcaga ttagacgacg taggtatgcc      60
cgcccatact accgcagacg tcacaacagg cgataccgcc ggagacgtag atacttccgc     120
agacgccgtt tctcgaccaa tagaatttac actatcagat tcaaacgcca attcaaattc     180
gaaattcaaa agcaaaccac cagtactggc caagtaattt ggaatgctga ctacataacc     240
tttgcattgt cagacttcct agcaacagcg ccaaacccac atacactaaa tttcgaagac     300
taccggatta aattagctaa aatggaattg aggcccacat ggggccacta cacaattagt     360
gcagacggat tcggccacac ggccataatc caagattcca gaataactaa atttaaaact     420
acttcagacc aaaatcaaga cccggtggct cctttcgacg gtgcaaaaaa gtggtatgtt     480
gccaggggat tcaaacgcct cctcagaccg aaacctcaaa taactataga tgacctgacc    540
actgcgaacc agtctgcggc attgtggcta acagcgcca ggaccggctg gatcccacta      600
caaggaggac ccaatgcggc aggagcgaac gtcaagcact acggccttgc attcagcttc     660
cctcagccag aagtgaaaat cacttatgta tgcgagctca ctctgtatgt tcaattccgt     720
cagtttgccc ccaacaatcc cagtacttaa                                     750

<210> SEQ ID NO 6
<211> LENGTH: 249
<212> TYPE: PRT
<213> ORGANISM: Psittacine Beak and Feather Disease Virus

<400> SEQUENCE: 6
```

Leu Trp Gly Thr Ser Asn Cys Ala Cys Ala Ile Phe Gln Ile Arg
1               5                   10                  15

Arg Arg Tyr Ala Arg Pro Tyr Tyr Arg Arg His Asn Arg Arg Tyr
            20                  25                  30

Arg Arg Arg Arg Tyr Phe Arg Arg Arg Phe Ser Thr Asn Arg
        35                  40                  45

Ile Tyr Thr Ile Arg Phe Lys Arg Gln Phe Lys Phe Glu Ile Gln Lys
50                  55                  60

Gln Thr Thr Ser Thr Gly Gln Val Ile Trp Asn Ala Asp Tyr Ile Thr
65                  70                  75                  80

Phe Ala Leu Ser Asp Phe Leu Ala Thr Ala Pro Asn Pro His Thr Leu
            85                  90                  95

Asn Phe Glu Asp Tyr Arg Ile Lys Leu Ala Lys Met Glu Leu Arg Pro
            100                 105                 110

Thr Trp Gly His Tyr Thr Ile Ser Ala Asp Gly Phe Gly His Thr Ala
            115                 120                 125

Ile Ile Gln Asp Ser Arg Ile Thr Lys Phe Lys Thr Thr Ser Asp Gln
130                 135                 140

Asn Gln Asp Pro Val Ala Pro Phe Asp Gly Ala Lys Lys Trp Tyr Val
145                 150                 155                 160

Ala Arg Gly Phe Lys Arg Leu Leu Arg Pro Lys Pro Gln Ile Thr Ile
                165                 170                 175

Asp Asp Leu Thr Thr Ala Asn Gln Ser Ala Ala Leu Trp Leu Asn Ser
            180                 185                 190

Ala Arg Thr Gly Trp Ile Pro Leu Gln Gly Gly Pro Asn Ala Ala Gly
            195                 200                 205

Ala Asn Val Lys His Tyr Gly Leu Ala Phe Ser Phe Pro Gln Pro Glu
            210                 215                 220

Val Lys Ile Thr Tyr Val Cys Glu Leu Thr Leu Tyr Val Gln Phe Arg
225                 230                 235                 240

Gln Phe Ala Pro Asn Asn Pro Ser Thr
            245

<210> SEQ ID NO 7
<211> LENGTH: 21
<212> TYPE: DNA
<213> ORGANISM: Artificial Sequence
<220> FEATURE:
<223> OTHER INFORMATION: Beak and Feather Disease Virus SCF primer

<400> SEQUENCE: 7
tcaaggccac gtgtcttgtc c                                          21

<210> SEQ ID NO 8
<211> LENGTH: 32
<212> TYPE: DNA
<213> ORGANISM: Artificial Sequence
<220> FEATURE:
<223> OTHER INFORMATION: Beak and Feather Disease Virus SCR primer

<400> SEQUENCE: 8
tccaggtacc ttactaggtg gggttggggt tg                              32

<210> SEQ ID NO 9
<211> LENGTH: 19
<212> TYPE: DNA
<213> ORGANISM: Artificial Sequence
<220> FEATURE:
<223> OTHER INFORMATION: Chen6560F forward primer -continued

```
<400> SEQUENCE: 9
gatccggcat gcactgatc                                                    19

<210> SEQ ID NO 10
<211> LENGTH: 20
<212> TYPE: DNA
<213> ORGANISM: Artificial Sequence
<220> FEATURE:
<223> OTHER INFORMATION: CM-terX reverse primer

<400> SEQUENCE: 10
gaacctcgtc attgatggac                                                   20
```